(12) United States Patent
Veldman et al.

(10) Patent No.: US 8,430,912 B2
(45) Date of Patent: Apr. 30, 2013

(54) DYNAMIC STABILIZATION ROD

(75) Inventors: Michael S. Veldman, Memphis, TN (US); Henry Keith Bonin, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 754 days.

(21) Appl. No.: 12/114,837

(22) Filed: May 5, 2008

(65) Prior Publication Data

US 2009/0275983 A1 Nov. 5, 2009

(51) Int. Cl.
 *A61B 17/70* (2006.01)
(52) U.S. Cl.
 USPC ......................................................... 606/257
(58) Field of Classification Search .................. 606/246, 606/254–256, 257, 259–260, 60, 261, 262–275
 See application file for complete search history.

(56) References Cited

U.S. PATENT DOCUMENTS

| | | | |
|---|---|---|---|
| 6,099,528 A * | 8/2000 | Saurat | 606/254 |
| 7,326,210 B2 * | 2/2008 | Jahng et al. | 606/86 A |
| 2003/0191470 A1 | 10/2003 | Ritland | |
| 2005/0131405 A1 | 6/2005 | Molz et al. | |
| 2005/0171540 A1 | 8/2005 | Lim et al. | |
| 2005/0177157 A1 | 8/2005 | Jahng | |
| 2005/0203516 A1 | 9/2005 | Biedermann et al. | |
| 2005/0203517 A1 | 9/2005 | Jahng et al. | |
| 2007/0190230 A1 * | 8/2007 | Trieu et al. | 427/2.24 |
| 2008/0177388 A1 * | 7/2008 | Patterson et al. | 623/17.16 |
| 2008/0183212 A1 * | 7/2008 | Veldman et al. | 606/254 |
| 2008/0183213 A1 * | 7/2008 | Veldman et al. | 606/257 |
| 2008/0234746 A1 * | 9/2008 | Jahng et al. | 606/278 |
| 2008/0300633 A1 * | 12/2008 | Jackson | 606/257 |
| 2009/0112267 A1 * | 4/2009 | Atkinson et al. | 606/279 |
| 2009/0131981 A1 * | 5/2009 | White | 606/246 |
| 2009/0216277 A1 * | 8/2009 | Tornier et al. | 606/250 |
| 2009/0234388 A1 * | 9/2009 | Patterson et al. | 606/246 |
| 2009/0259257 A1 * | 10/2009 | Prevost | 606/255 |

\* cited by examiner

*Primary Examiner* — Eduardo C Robert
*Assistant Examiner* — Michelle C Eckman

(57) ABSTRACT

A spinal stabilization rod includes a first rod portion having a proximal end and a distal end and having a first cross-sectional area. The second rod portion extends from the distal end of the first rod portion and has a second minimum cross-sectional area smaller than the first cross-sectional area. The second rod portion is formed of a first material and a different second material, with the first material being more resistant in shear than the second material. The implant also includes a slider portion disposed about and movable relative to the second rod portion.

24 Claims, 4 Drawing Sheets

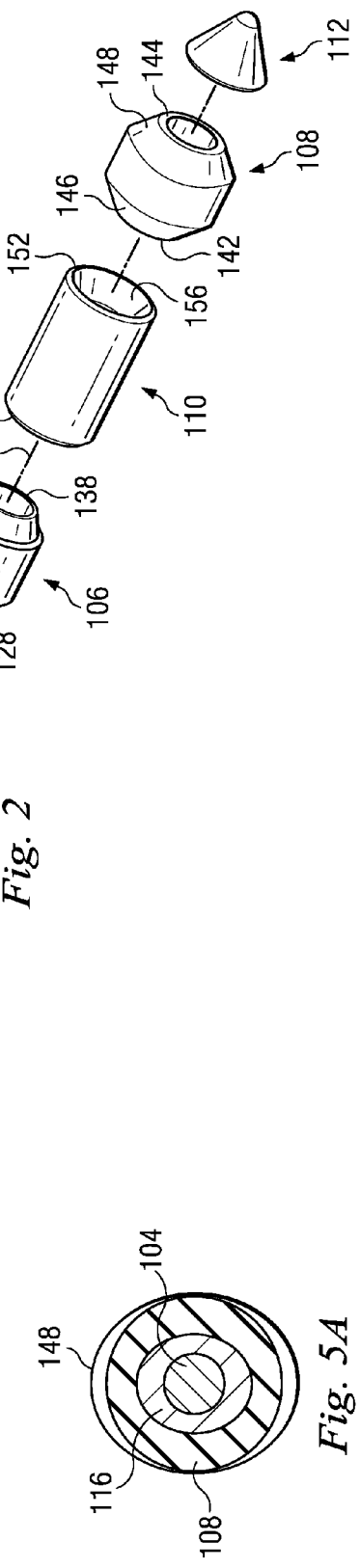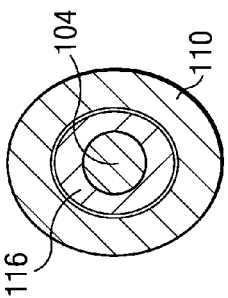

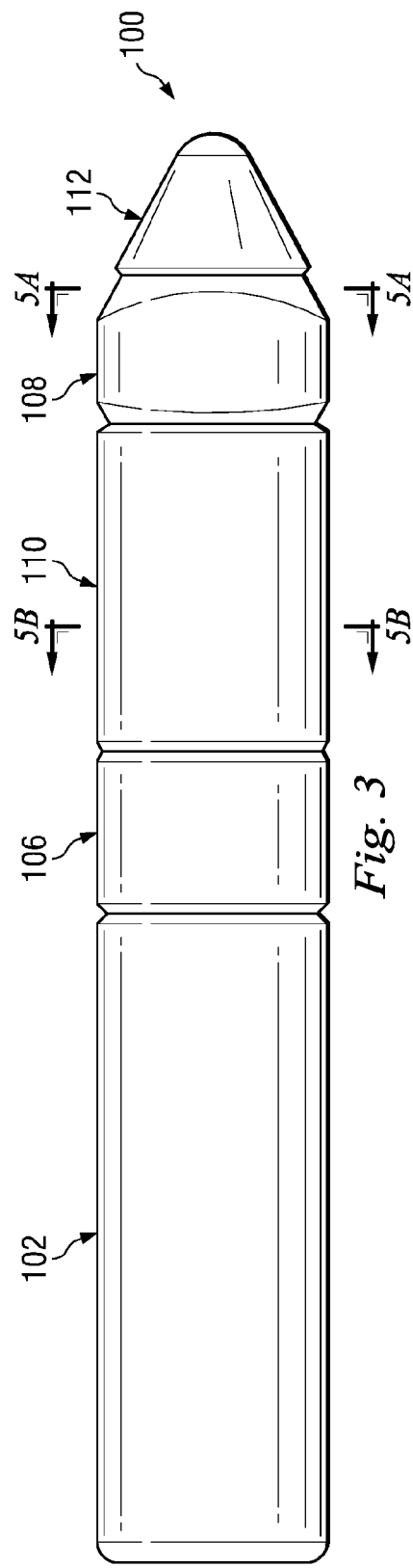
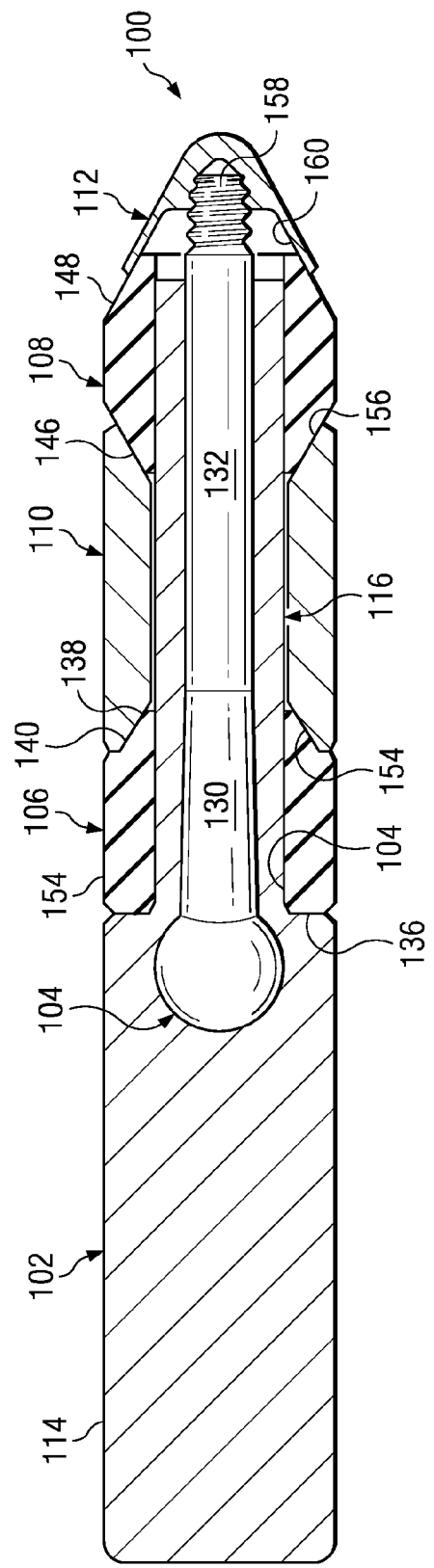

DYNAMIC STABILIZATION ROD

FIELD OF THE INVENTION

The present disclosure relates to an implant for preserving motion between vertebrae, and more particularly, to a device for improving posterior spinal function with a pedicle-based dynamic stabilization rod implant.

BACKGROUND

Severe back pain, limited motion, and nerve damage may be caused by injured, degraded, or diseased spinal anatomy. Affected spinal joints, and particularly discs and ligaments, can be difficult to treat externally and may necessitate surgery.

In some surgical treatments, posterior rods may be attached to variously affected spinal levels to inhibit or limit motion. Some posterior rods are rigid rods which substantially, if not totally, eliminate freedom of motion for bending in flexion and extension. Other important motions may similarly be eliminated.

During implantation, treating physicians frequently use rigid bone screws or anchors to attach the rods to some vertebrae, and because perfectly aligning the rods and screws can be difficult, use non-locking screws to attach the rods to other vertebrae. Accordingly, the treating physician must decide in advance or during the procedure which type of screw to use in each location.

The present disclosure is directed to a system that overcomes one or more of the shortcomings of the prior art by providing dynamic stabilization to vertebrae of a spinal column.

SUMMARY

In one exemplary aspect, the present disclosure is directed to a spinal stabilization implant that cooperates with pedicle screws to provide dynamic stabilization between upper and lower vertebrae in a spinal column. The implant includes a first rod portion having a proximal end and a distal end and having a first cross-sectional area. It also includes a second rod portion having a proximal end and a distal end. The second rod portion extends from the distal end of the first rod portion and has a second cross-sectional area smaller than the first cross-sectional area. The second rod portion is formed of a first material and a different second material, with the first material being more resistant in shear than the second material. The implant also includes a slider portion disposed about and movable relative to the second rod portion. The slider portion is sized and configured to attach to a pedicle screw.

In another exemplary aspect, the present disclosure is directed to a spinal stabilization implant that cooperates with pedicle screws to provide dynamic stabilization between upper and lower vertebrae in a spinal column. The implant includes a first rod portion having a proximal end and a distal end. A damper is disposed about the first rod portion and includes a first tapering surface. A slider portion is disposed about and movable relative to the second rod portion. The slider portion includes a second tapering surface. The slider portion and the damper at least partially overlap each other such that the first tapering surface interfaces with the second tapering surface.

In one aspect, the damper is formed of a material having compressive properties that limit movement of the slider portion along the first rod portion by: a. providing resistance to movement of the slider portion in the axial direction; and b. increasing the frictional resistance of the damper along the first rod portion as a result of radial deformation.

In yet another exemplary aspect, the present disclosure is directed to a surgical implant including a rod portion and a slider disposed about the rod portion. The slider is to connect with a pedicle screw. A dampening system includes a first damper and a second damper. The first damper is disposed about the rod portion to inhibit axial displacement of the slider along the rod portion in a first axial direction. The second damper is disposed about the rod portion to inhibit axial displacement of the slider along the rod in a second opposing axial direction. These first and second dampers are arranged so that under a first load applied in the first axial direction, the first damper inhibits displacement to a first distance, and under an equivalent load applied in the second direction, the second damper inhibits displacement to a second distance different than the first distance.

In yet another exemplary aspect, the present disclosure is directed to a spinal stabilization implant including a first rod portion having a first cross-sectional area and a second rod portion extending from the first rod portion. The second rod portion has a second cross-sectional area different than the first cross-sectional area. The second rod portion includes an inner core formed of a first material and an outer rod portion surrounding the inner core. The outer rod portion is formed of a second material different than the first material. The implant includes a damper disposed about the first rod portion. The damper includes a first tapering surface facing radially away from the second rod portion. A slider portion is disposed about the first rod portion adjacent the damper. The slider portion includes a second tapering surface facing radially inwardly toward the second rod portion. The first and second tapering surfaces are disposed to interface with each other.

These and other features will become apparent from the following description.

BRIEF DESCRIPTION OF THE DRAWINGS

FIG. 2 is an illustration of an exploded view of the dynamic rod implant according to one exemplary embodiment.

FIG. 3 is an illustration of a side view of the dynamic rod implant according to one exemplary embodiment.

FIG. 4 is an illustration of a cross-section view of the exemplary dynamic rod implant shown in FIG. 3.

FIGS. 5A and 5B are illustrations of cross-sectional views of the exemplary dynamic rod implant taken along the lines 5A-5A and 5B-5B respectively in FIG. 3.

DETAILED DESCRIPTION

Figure 1:
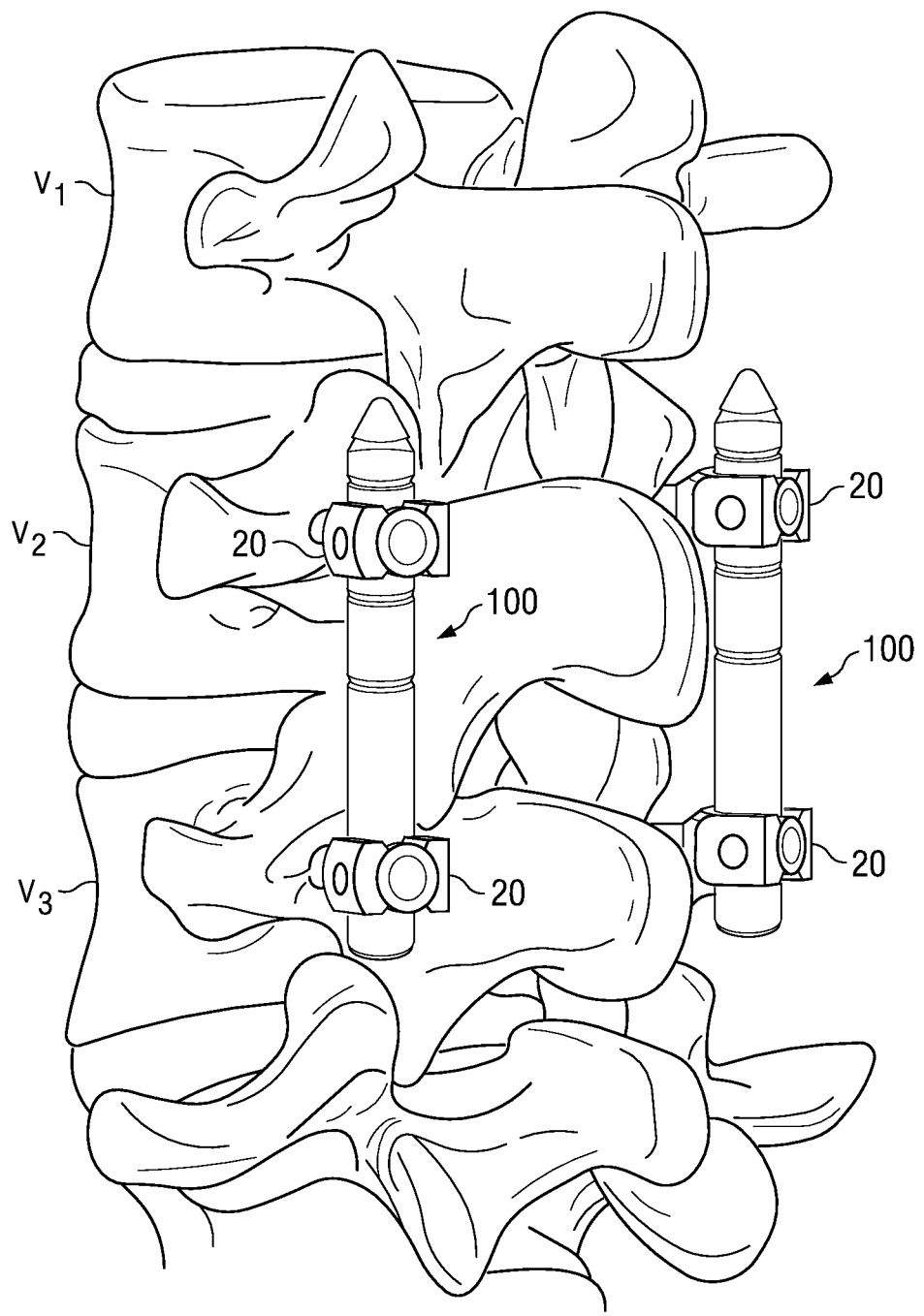
FIG. 1 is an illustration of an isometric view of an exemplary dynamic rod implant according to one embodiment installed on pedicles of adjacent vertebrae.

For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Generally, the present disclosure relates to an implant for preserving motion between vertebrae, and more particularly, to a surgical implant that cooperates with pedicle screws to provide dynamic stabilization between upper and lower vertebrae in a spinal column. In some embodiments, these implants allow for axial (or translational) motion and allow for bending (or angular) motion. The axial motion is regulated using dynamic bumpers or dampers and the bending or angular motion is regulated by controlling implant stiffness with an implant core and through a damper arrangement. Because the implants provide bending motion as well as axial motion, a treating physician may choose to forgo choosing between locking and non-locking pedicle screws, but may have the option of using only locking pedicle screws, while still providing for the desired axial and bending movement. This may simplify the implantation process and the device also may more closely approximate the natural function of the motion segments than prior devices.

In addition, the dampers are shaped to provide desired motion characteristics under loads applied by the vertebrae. For example, in some embodiments, these dampers permit more axial movement in flexion of the spine (distance between the pedicles increases) than in extension of the spine (when distance between the pedicles decreases). The dampers are shaped to cooperate with a slider to control axial compression of the damper using both compression and deformation characteristics. In addition, the dampers provide some dampening to movement of the slider in shear.

Turning now the figures, FIG. 1 shows an exemplary dynamic rod implant 100 implanted along a representative section of a patient's spine. The representative section is shown as a posterior isometric view of a portion of the lumbar region and comprises vertebrae labeled $V_1$, $V_2$, and $V_3$. Pedicle screws 20 are shown attached through respective pedicle portions of vertebrae $V_2$ and $V_3$. The pedicle screws 20 may be any conventional pedicle screws and may include dynamic pedicle screws, locking pedicle screws, or a combination of both.

FIGS. 2-4 show the exemplary implant 100 in greater detail. FIG. 2 shows the components of the implant in an exploded form, and FIGS. 3 and 4 show the implant 100 assembled. The implant 100 generally extends along a longitudinal axis 101 and includes a base 102, a core 104, dampers 106, 108, a slider 110, and a cap 112.

The base 102 includes a proximal rod portion 114 having an elliptical cross-section and a distal rod portion 116 having a smaller elliptical cross-section. Thus, the cross-sectional area of the proximal rod portion 114 is greater than the cross-sectional area of the distal rod portion 116. The proximal rod portion 114 includes a proximal end 118 and a distal end 120. The outer surface cooperates with a pedicle screw to secure the proximal rod portion 114 to the vertebral column. The distal rod portion 116 also includes a proximal end 122 and a distal end 124, with the proximal end 122 of the distal rod portion 116 attached to the distal end 120 of the proximal rod portion 114.

The core 104 extends between a proximal end 126 and a distal end 128. It cooperates with at least the distal rod portion 116 to control the stiffness of the distal rod portion 116 and to increase or decrease the distal rod portion's resistance to shear stress. In the exemplary embodiment shown, the core 104 has an axial length slightly greater than the length of the distal rod portion 116 so that it protrudes outwardly from the distal end portion 124 of the distal rod portion 116 and so that it extends at least partially into the proximal rod portion 114, as best shown in FIG. 4. Also in the example shown, the proximal end acts as a bulbous anchor. A tapering segment 130 extends from the bulbous proximal end 126, and narrows toward the distal end 128. In the exemplary embodiment shown, a cylindrical segment 132 extends from the tapering segment 130 toward the distal end 128. Threading 134 disposed at the distal end 128 of the core 104 permits attachment to the cap 112.

Still referring to FIG. 4, the core 104 is embedded in the base 102. In some examples, the core 104 is formed of a first relatively rigid material and the base 102 is formed of a second relatively less rigid material. In some examples, the core 104 is formed of a metal material, such as for example, titanium, and the base is formed of a polymeric material, such as for example, PEEK. It is noted however, that any suitable material may be selected for either the core or the base, including, without limitation, polyetheretherketone (PEEK), polyethylene terephthalate (PET), polyester, polyetherketoneketone (PEKK), polylactic acid materials (PLA and PLDLA), polyaryletherketone (PAEK), carbon-reinforced PEEK, polysulfone, polyetherimide, polyimide, ultra-high molecular weight polyethylene (UHMWPE), cross-linked UHMWPE, and/or polycarbonate, cobalt-chromium alloys, titanium alloys, nickel titanium alloys, aluminum, stainless steel alloys, and/or NITINOL or other memory alloy, ceramic materials such as aluminum oxide or alumina, zirconium oxide or zirconium, compact of particulate diamond, and/or pyrolytic carbon, among other materials. In some examples, the core 104 is formed of a less rigid material and the base 102 is formed of a more rigid material.

Still referring to FIG. 4, the core 104 and the distal rod portion 116 may be sized so that the tapering segment 130 is disposed adjacent the interface or transition location of the proximal and distal rod portions 114, 116. In embodiments with a relatively stiffer core 104 and less stiff base 102, this tapering segment 130 strengthens and supports the transition location, compensating for weaknesses due to stress risers, and assists in shear resistance. The bulbous proximal end is substantially embedded in the proximal rod portion 114 of the base 102. This bulbous end acts as an anchor that resists pull-out or dislocation of the core 104 from the base 102, and to a lesser extent provides a pivot-point about which the distal rod portion 116 and core 104 may provide bending. Although shown as a spherical ball, the proximal end 126 may have any shape that may or may not act as an anchoring portion. In some embodiments, the core 104 may be pinned, welded, or otherwise fastened to the base 102.

Although the core 104 is disclosed as having a length less than that of the base 102, in some embodiments, the core 104 extends completely through the proximal and distal rod portions 114, 116, or partially through the base 102 as shown, but with a length longer or shorter than that shown. Furthermore, the core 104 may have alternative shapes. For example, in some embodiments, the core 104 may be cylindrical along nearly all its length. Other shapes and configurations are also contemplated.

The core 104 may be embedded in the base portion 102 using any number of methods or processes. In one example, the base 102 is over molded about the core 104. This may permanently secure the core 104 into the base 102. In some embodiments, the core may be introduced through the distal end 124 of the distal rod portion 104 or, alternatively, through another introduction region formed in the base 102.

The dampers 106, 108 are formed to fit about the distal rod portion 116 and provide dampening movement to the implant 100. The damper 106 is disposed adjacent the proximal rod portion 114 of the base 102 and the damper 108 is disposed toward the distal end of the distal rod portion 116. In the exemplary embodiment shown, the damper 106 includes a generally planar proximal end 136 and a tapering distal end portion 138. The damper 106 is sized to have an outer elliptical shape generally corresponding to the outer elliptical shape of the base member 102, and sized to have an elliptically-shaped inner bore that receives and permits axial movement along the distal rod portion 116. The tapering distal end portion 138 includes a tapering interface 140 that interfaces with the slider 110 as described further below.

The damper 108 is spaced from the damper 106 by the slider 110.

Like the damper 106, the damper 108 includes an outer elliptical shape generally corresponding in size to that of the base member 102, and includes an elliptical inner bore that receives and permits axial movement along the distal rod portion 116. The damper 108 includes first and second taper portions at both its proximal end 142 and its distal end 144. The taper portions include a tapering interface 146 that interfaces with the slider 110 and a tapering interface 148 that interfaces with the cap 112. FIG. 5A shows a cross-section taken through the bumper 108 along the lines 5A-5A in FIG. 3.

The dampers 106, 108 may be formed of any known biocompatible damper material, including, for example, polycarbonate-urethane, polyurethane, silicone, silicone-polyurethane, polyolefin rubbers, hydrogels, and the like. Other suitable elastic materials may include NITINOL or other superelastic alloys. Further, combinations of superelastic alloys and non-metal elastic materials also may be suitable.

The slider 110 is sized and shaped to interface with a pedicle screw and is disposed about the distal rod potion 116 between the dampers 106, 108. The exemplary slider 110 has an elliptical outer surface and an elliptical inner surface. Each of a proximal end 150 and a distal end 152 of the slider 110 includes tapering portions that form tapering interfaces 154, 156 that interface with the dampers 106, 108, respectively. Also, in some embodiments, the bore of the slider 110 may be sized larger than the size of the distal rod portion 116 so that the slider 110 may displace transversely relative to the distal rod portion 116. FIG. 5B shows a cross-section taken through the slider 110 along the lines 5B-5B in FIG. 3.

The slider 110 may be formed of the same material as the base 102, as the core 104, or of an alternative material. Because the slider 110 axially slides along the distal rod portion 116, the slider and the distal rod portion materials may be selected to minimize debris or wear. In one embodiment, the slider is formed of a titanium material while the distal rod portion 116 is formed of PEEK. Both the slider 110 and the distal rod portion 116 may undergo surface treatments or lubrication to provide an optimum interface. For example, either may be anodized, polished, case hardened, or undergo other treatment. In some embodiments, a medical grade lubrication also may be used to reduce friction and wear.

The cap 112 connects to the core 104 to secure the dampers 106, 108 and the slider 110 on the base 102. In the example shown, and best seen in FIG. 4, the cap 112 includes a threaded bore 158 that receives the threads 134 on the core 104. The cap 112 overlaps a portion of the damper 108 and includes a tapering interface 160 that interfaces with the tapering interface 148. Although the cap 112 is shown as threaded, the cap 112 may connect to the core 104, or alternatively the base 102, using any known method or system, including, for example, metal welding, laser welding, or sonic welding, gluing, snap-fitting, cam locking, slot or bayonet locking, crimping, gluing, and the like.

The drawings show the proximal rod portion 114 of the base 102 being formed substantially of a single material, while the distal rod portion 116 of the base 102, upon which the slider 110 operates, is formed of two or more materials. These two or more materials may combine to provide a stiffness that substantially corresponds to the stiffness of the proximal rod portion 114 despite the smaller cross-sectional area, or alternatively, may combine to provide a stiffness greater or less than the stiffness of the proximal rod portion 114. In some embodiments, the two materials provide flexibility to the implant 100, permitting the bending motion under applied shear loads.

Although shown as integral components, the proximal and distal rod portions 114, 116 may be separate components, and in some embodiments, may be separate or different materials. For example, in some embodiments, the core 104 may be embedded or fixed into the proximal rod portion 114, and the distal end portion 116 may then be introduced over the rod and held in place by the cap 112.

Returning now to FIG. 1, the implant 100 attaches to the vertebrae using the pedicle screws 20. These connect to the implant at the base 102 and at the slider 110. It is contemplated that implant 100 may be compatible with pedicle screws or other anchors from a variety of manufacturers. When attached to the pedicle screws, the implant 100 provides both axial (or translational) motion and bending (or angular) motion. When the upper vertebra V2 moves in flexion relative to the lower vertebra V3, the slider moves toward the distal or cap-end of the implant 100. Similarly, when the upper vertebra V2 moves in extension relative to the lower vertebra V3, the slider moves toward the proximal rod portion 114.

The elliptical nature of the proximal and distal rod portions 114, 116 of the base 102 results in opposing sides having a thickness or volume of material greater than the thickness of material on the intermediate sides, as can be seen in FIGS. 5A and 5B. This unequal distribution of material permits varying amounts of bending and deformation depending on the direction of the bend relative to the elliptical shape. For example, the implant 100 may be relatively more stiff when flexed in the direction having more material and relatively less stiff when flexed in the direction having less material. Accordingly, in some embodiments, the implant 100 is implanted within a patient so that the sides having more material are disposed on one or both of a posterior and anterior side and the sides having less material are disposed on one or both of the lateral sides of the implant. Alternatively, the implant may be implanted so that the sides having more material are disposed on the lateral sides and the sides having less material face the anterior and posterior directions. Other arrangement also are contemplated.

In addition, although described as having components with an elliptical-shaped surface, in other embodiments, the implant 100 includes a circular cross-section or cylindrical outer surface, with all the components being correspondingly formed. In yet other embodiments, the implant 100 includes components having a rectangular shaped cross-section. Other shapes also are contemplated. In some embodiments, the core 104 has an elliptical cross-section or other shaped cross-section.

Depending on the direction of movement, either the damper 106 or the damper 108 provides dampening in two modes: axial compression and radial compression. The axial compression occurs as the slider 110 axially compresses the damper. As the damper is compressed, its resistance to axial compression increases. The radial compression is due to the overlapping arrangement of the tapering interfaces of the slider 110 and the dampers. The relevant slider tapering interface 154, 156 acts on the tapering interface of the relevant damper. These tapering interfaces force the damper to compress radially. In addition to dampening simply by the nature of the elasticity of the damper, the damper is forced into contact with, or more tightly squeezes around the distal rod portion 116. This increases the friction between the damper and the distal rod portion 116, providing increased resistance to movement, and thereby dampening the movement. Embodiments with elliptical cross-sections may provide unequal radial compression against the distal rod portion 116, while embodiments with circular cross-sections may provide equal radial compression against the distal rod portion.

The bending motion of the implant is permitted based on two interacting arrangements. First, the smaller cross-sectional area distal rod portion 116 and the core 104 permit controlled stiffness based on the size and selection of the core material. This provides the flexibility of the distal rod portion 116. Second, the overlapping arrangement of the dampers 106, 108 and slider 110 (with the dampers 106, 108 partially disposed between the slider 110 and the distal end portion 116) permits the slider 110 to displace transverse the implant axis 101 by compressing the dampers in a transverse direction. Thus, the dampers 106, 108 are arranged to dampen slider movement in the direction transverse to the implant axis 101.

In some embodiments, the two dampers 106, 108 are formed or selected to provide a first level of dampening in spinal flexion and a second level of dampening in spinal extension. Therefore, the range of spinal motion permitted by the implant 100 more closely reflects the motion of a healthy spine because a healthy spine permits greater motion in spinal flexion than in spinal extension.

Figure 6A:
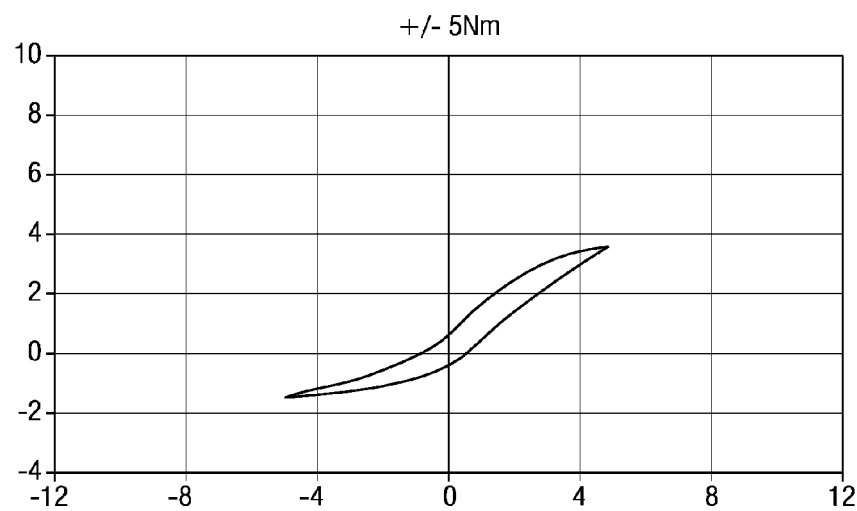
FIGS. 6A-6C are graphical representations of axial displacement over applied loads in both spinal extension and spinal flexion.
Figure 6B:
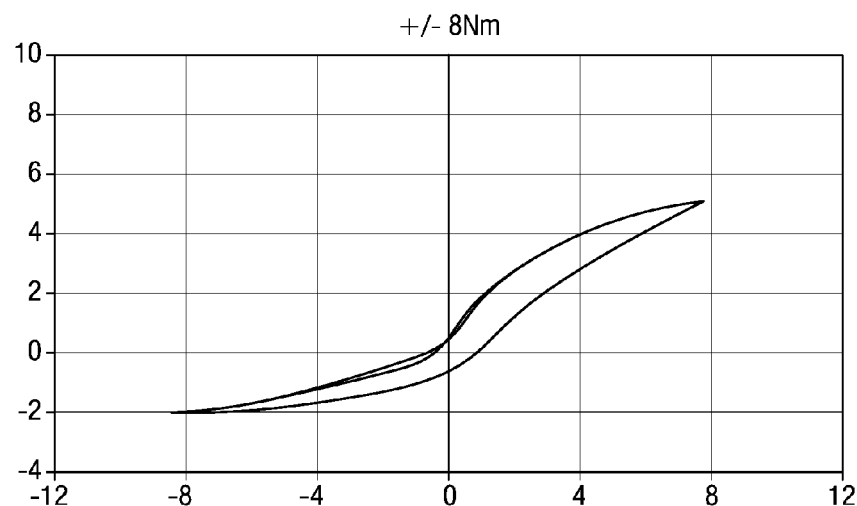
Figure 6C:
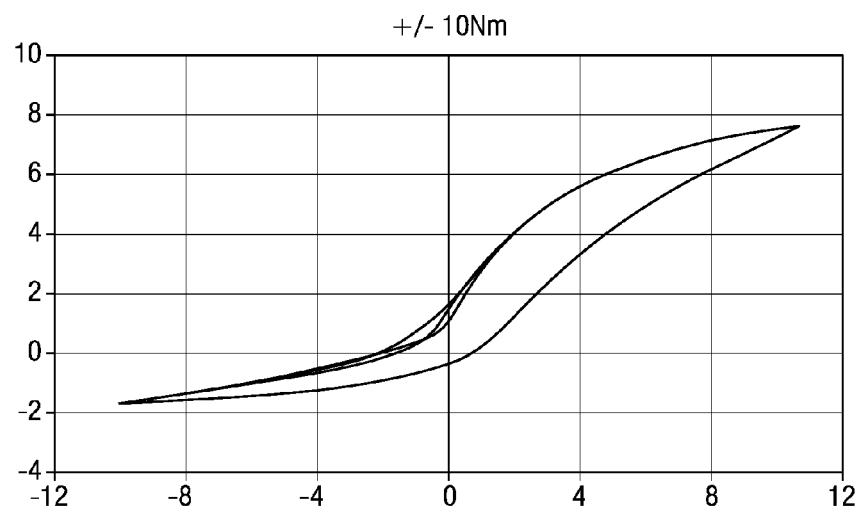

FIGS. 6A-6C are graphs showing implant response to exemplary levels of torque applied in accordance with the disclosure herein. Referring first to FIG. 6A, under loading of 5 Nm, the implant permitted axial displacement of nearly four degrees in spinal flexion and nearly two degrees in spinal extension. FIG. 6B shows that under loading of 8 Nm, the implant permitted axial displacement of about five degrees in spinal flexion; an increase of nearly 1.5 degrees. However, in spinal extension, the displacement changed only slightly. FIG. 6C shows a similar outcome of increasing spinal flexion but not a substantial change in spinal extension. In FIG. 6C, under loading of 10 Nm, the implant permitted axial displacement of nearly eight degrees in spinal flexion and still fell around two degrees in spinal extension.

In some embodiments, the dampers 106, 108 are formed of different materials having different stiffness to achieve the plots shown in FIGS. 6A-6B. In other embodiments, the dampers 106, 108 are formed of different sizes, having different lengths, different diameters, or different shapes.

Although described as a single level dynamic stabilization rod, the implant 100 may extend multiple levels. For example, in some embodiments, the proximal rod portion may have a length permitting it to extend along the posterior of one or more additional vertebrae. In addition, in some embodiments, the distal rod portion may be extended such that the implant may include one or more additional sliders and dampers between the damper 108 and the cap 112. Other arrangements also are contemplated.

Certain features and benefits are discussed with respect to certain embodiments. It is contemplated that any feature disclosed on any specific embodiment may be utilized on any other embodiment.

The implant 100 is formed so that the distal rod portion 114 provides a desired level of flexibility based upon the combination of the base portion 102 and the core 104. The materials used to form the distal rod portion are selected to cooperatively achieve the desired flexibility. During manufacturing of one exemplary implant, the core 104 is formed of a first material by, for example, machining or molding. The core 104 may then be placed within a mold for the base 102. A polymeric material forming the base 102 may over-mold the core 102, embedding the core within the base 102. In some embodiments, the polymeric material is a thermo-setting polymer, although other materials may be used. The first damper 106 may be separately molded and placed over the distal rod portion 116. The slider 110 may be formed by machining and its inner surface may be highly polished. It too may be placed over the distal rod portion 116. The second damper 108 may be molded to a desired shape and placed over the distal rod portion 116. Finally, the cap 112 may be formed and attached to the core member. In some embodiments, the cap 112 is attached to the base member 102.

Multiple methods of accessing the surgical sight to accomplish the purposes of this disclosure are contemplated. In one embodiment, a posterior surgical approach is used. An operating physician attaches the pedicle screws to the vertebrae as known in the art. He or she may then introduce the implant 100 to the surgical site. Once pedicle screw may be attached to the slider 110 and another to the proximal rod portion 114. The surgical site may then be cleaned and closed.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternatives are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

We claim:

1. A spinal stabilization implant that cooperates with pedicle screws to provide dynamic stabilization between upper and lower vertebrae in a spinal column, comprising:

a first rod portion extending along a longitudinal axis and having a proximal end and a distal end, the distal end having a first cross-sectional area, the first rod portion further including an inner surface defining a first bore, the first rod portion being formed of a first material;

a second rod portion extending along the longitudinal axis and having a proximal end and a distal end comprising an opening, the second rod portion extending from the distal end of the first rod portion, the second rod portion having a second cross-sectional area less than the first cross-sectional area and being formed of the first material such that the second rod portion has the same resistance to shear as the first rod portion, the second rod portion including an inner surface defining a second bore in communication with the first bore and the opening;

a core having a proximal end positioned in the first bore and a distal end extending through the opening in the second rod portion, the core being formed of a second material that is more resistant in shear than the first material to control the stiffness of the second rod portion;

a slider portion engageable with the second rod portion, the slider portion being disposed about and movable relative to the second rod portion, the slider portion being sized and configured to attach to a pedicle screw;

a first damper disposed about the second rod portion; and a second damper disposed about the second rod portion, the second damper being separate from and disposed in non-engagement with the first damper.

2. The surgical implant of claim 1, wherein the first material is a metal material and the second material is a polymeric material molded over the metal material.

3. The surgical implant of claim 1, wherein the the second rod portion and the core are concentrically aligned along the longitudinal axis and an outer diameter of the core increases along the longitudinal axis and the shape of the outer surface of the second rod portion does not substantially change along the longitudinal axis.

4. The surgical implant of claim 1, wherein the core extends from an anchor portion disposed in the first rod portion adjacent the second rod portion.

5. The surgical implant of claim 1, wherein the first and second dampers each having a tapering surface that interfaces with and overlaps with a portion of the slider portion.

6. The surgical implant of claim 5, wherein the slider portion comprises a tapering surface interfacing with the tapering surfaces of the first and second dampers.

7. The surgical implant of claim 6, wherein the tapering surface of the first damper faces away from the second rod portion and wherein the tapering surface of the slider faces toward the second rod portion.

8. The surgical implant of claim 5, wherein the first and second damper are each formed of a material having compressive properties that limit movement of the slider portion along the second rod portion by:
 a. providing resistance to movement of the slider portion in the axial direction; and
 b. increasing the frictional resistance of the damper along the first rod portion as a result of radial deformation.

9. The surgical implant of claim 1, wherein the proximal end of the core defines a bulbous anchor, the core including a tapering segment between the anchor and the distal end of the core.

10. The surgical implant of claim 9, wherein a proximal end of the tapering segment is disposed in the first bore and a distal end of the tapering segment is disposed in the second bore.

11. A spinal stabilization implant that cooperates with pedicle screws to provide dynamic stabilization between upper and lower vertebrae in a spinal column, comprising:
 a first rod portion extending along a longitudinal axis and having a proximal end and a distal end, the distal end having a first cross-sectional area, the first rod portion further including an inner surface defining a first bore, the first rod portion being formed of a first material;
 a second rod portion extending along the longitudinal axis and having a proximal end and a distal end comprising an opening, the first rod portion formed of the first material such that the second rod portion has the same resistance to shear as the first rod portion the first rod portion including an inner surface defining a second bore in communication with the first bore and the opening;
 a core positioned in the first and second bores, the core being formed of a second material that is more resistant in shear than the first material to control the stiffness of the second rod portion;
 a damper including a first damper disposed about the second rod portion and a second damper disposed about the second rod portion, the second damper being separate from and disposed in non-engagement with the first damper, the first damper including a first tapering surface; and
 a slider portion engageable with the second rod portion, the slider portion being disposed about and movable relative to the second rod portion, the slider portion including a second tapering surface, the slider portion and the first damper at least partially overlapping each other such that the first tapering surface interfaces with the second tapering surface.

12. The surgical implant of claim 11, wherein at least one of the first and second damper is formed of a material having compressive properties that limit movement of the slider portion along the second rod portion by:
 a. providing resistance to movement of the slider portion in the axial direction; and
 b. increasing the frictional resistance of the at least one damper along the first rod portion as a result of radial deformation.

13. The surgical implant of claim 11, wherein the core has a circular cross-sectional shape; and the first and second rod portions have an elliptical cross-sectional shape.

14. The surgical implant of claim 13, wherein the core and the second rod portion are concentrically aligned along the longitudinal axis and an outer diameter of the core increases along the longitudinal axis and the shape of the outer surface of the second rod portion does not substantially change along the longitudinal axis.

15. The surgical implant of claim 11, wherein the core includes a proximal end defining an anchor portion disposed in the first bore and a distal end opposite the proximal end disposed in the second bore and extending through the opening in the second rod portion.

16. The surgical implant of claim 11, wherein the second damper has a tapering surface, and wherein the slider portion includes a tapering surface disposed to interface with the tapering surface of the second damper.

17. The surgical implant of claim 16, wherein the first and second dampers have different compression characteristics.

18. The surgical implant of claim 11, wherein the tapering surface of the first damper tapers at an angle along first and second ends of the first damper.

19. A surgical implant for providing dynamic stabilization between upper and lower vertebrae in a spinal column, comprising:
 a rod extending along a longitudinal axis and having a first rod portion and second rod portion, the first rod portion including an inner surface defining a first bore, the first rod portion being formed of a first material, the first rod portion having a first cross-sectional area and the second rod portion having a different cross-sectional area, the second rod portion being formed of the first material and having the same resistance to shear as the first rod portion, the second rod portion including an inner surface defining a second bore in communication with the first bore and an opening in a distal end of the second rod portion;
 a core having a proximal end positioned in the first bore and a distal end extending through the opening in the second rod portion, the core being formed of a second material that is more rigid than the first material to control the stiffness of the second rod portion, the distal end of the core including a thread form configured to engage a thread form on a cap;
 a slider engageable with the second rod portion, the slider being disposed about the second rod portion and configured to connect with a pedicle screw; and
 a dampening system comprising a first damper and a second damper, the second damper being separate from and disposed in non-engagement with the first damper, the first damper being disposed about the second rod portion to inhibit axial displacement of the slider along the second rod portion in a first axial direction, the second damper being disposed about the second rod portion to inhibit axial displacement of the slider along the second rod portion in a second opposing axial direction, the first and the second dampers being arranged so that under a first load applied in the first axial direction, the first damper inhibits displacement to a first distance, and under an equivalent load applied in the second direction, the second damper inhibits displacement to a second distance different than the first distance.

20. The surgical implant of claim 19, wherein the first and second dampers have a different shape.

21. The surgical implant of claim 20, wherein the first and second dampers are formed of different materials.

22. A spinal stabilization implant that cooperates with pedicle screws to provide dynamic stabilization between upper and lower vertebrae in a spinal column, comprising:
a first rod portion extending along a longitudinal axis and having a first cross-sectional area, the first rod portion including an inner surface defining a first bore, the first rod portion being formed of a first material;
a second rod portion extending along the longitudinal axis from the first rod portion, the second rod portion having a second cross-sectional area different than the first cross-sectional area, the second rod portion formed of the first material and having the same resistance to shear as the first rod portion, the second rod portion including an inner surface defining a second bore in communication with the first bore and an opening in a distal end of the second rod portion;
an inner core extending along the longitudinal axis and formed of a second material, the second material being more resistant in shear than the first material to control the stiffness of the second rod portion, a proximal end of the core being positioned in the first bore and a distal end of the core extending through the opening, the distal end of the core including a thread form configured to engage a thread form on a cap,
a first damper disposed about the second rod portion and a second damper disposed about the second rod portion, the second damper being separate from and disposed in non-engagement with the first damper, the first damper including a first tapering surface facing radially away from the second rod portion; and
a slider portion disposed about and being engageable with the second rod portion adjacent the first damper and the second damper, the slider portion including a tapering surface facing radially inwardly toward the second rod portion, the tapering surfaces being disposed to interface with each other, the slider portion being sized and shaped to attach to a pedicle screw.

23. The surgical implant of claim 22, wherein the second damper includes a tapering surface facing radially away from the second rod portion, and wherein the slider portion comprises a second tapering surface facing radially inwardly toward the second rod portion, the second tapering surface and the tapering surface of the second damper being disposed to interface with each other.

24. The surgical implant of claim 23, wherein the second damper includes a tapering surface at an end opposing the second tapering surface facing radially away from the second rod portion.

* * * * *